(12) United States Patent
Tice et al.

(10) Patent No.: US 7,034,304 B2
(45) Date of Patent: Apr. 25, 2006

(54) CHAMBER FOR GAS DETECTOR

(75) Inventors: Lee D. Tice, Bartlett, IL (US); Dragan P. Petrovic, Geneva, IL (US)

(73) Assignee: Honeywell International, Inc., Morristown, NJ (US)

( * ) Notice: Subject to any disclaimer, the term of this patent is extended or adjusted under 35 U.S.C. 154(b) by 127 days.

(21) Appl. No.: 10/627,361

(22) Filed: Jul. 25, 2003

(65) Prior Publication Data

US 2005/0017206 A1     Jan. 27, 2005

(51) Int. Cl.
G01N 21/00 (2006.01)
G01N 15/06 (2006.01)

(52) U.S. Cl. ............ 250/343; 250/573; 250/339.13; 356/437

(58) Field of Classification Search ........ 250/343, 250/345, 573, 252.1, 338.5, 339.09, 339.13; 356/437, 438, 439
See application file for complete search history.

(56) References Cited

U.S. PATENT DOCUMENTS

| | | | |
|---|---|---|---|
| 4,008,394 A * | 2/1977 | Risgin et al. ............ 250/345 |
| 4,500,207 A | 2/1985 | Maiden | |
| 4,520,265 A | 5/1985 | Griggs et al. | |
| 4,578,762 A | 3/1986 | Wong | |
| 4,709,150 A | 11/1987 | Burough et al. | |
| 4,772,790 A | 9/1988 | Aldridge | |
| 5,041,723 A | 8/1991 | Ishida et al. | |
| 5,163,332 A | 11/1992 | Wong | |
| 5,220,402 A | 6/1993 | Harvey | |
| 5,444,249 A | 8/1995 | Wong | |
| 5,488,227 A | 1/1996 | Sweet | |
| 5,585,635 A | 12/1996 | Graham | |
| 5,721,430 A | 2/1998 | Wong | |
| 5,781,306 A | 7/1998 | Hartig et al. | |
| 5,811,812 A | 9/1998 | Williams et al. ............ 250/343 |
| 5,834,777 A | 11/1998 | Wong | |
| 5,850,354 A | 12/1998 | Bramley et al. | |
| 5,889,199 A | 3/1999 | Wong et al. | |
| 6,067,840 A * | 5/2000 | Chelvayohan et al. ....... 73/23.2 |
| 6,151,952 A | 11/2000 | Mathews et al. .......... 73/23.31 |
| 6,469,303 B1 | 10/2002 | Sun et al. .................. 250/343 |
| 6,528,420 B1 | 3/2003 | Tong et al. ................. 438/680 |
| 6,534,769 B1 * | 3/2003 | Graham ..................... 250/343 |
| 2001/0048079 A1 * | 12/2001 | Brunamoti et al. ......... 250/343 |
| 2002/0104967 A1 * | 8/2002 | Kouznetsov ........... 250/339.13 |

FOREIGN PATENT DOCUMENTS

JP       61281966 A     12/1986

* cited by examiner

Primary Examiner—David Porta
Assistant Examiner—Faye Polyzos
(74) Attorney, Agent, or Firm—Welsh & Katz, Ltd.

(57) ABSTRACT

A gas sensor, which could be a sensor of combustible gases, incorporates a diffusion chamber having symmetrical sensing and reference portions. A common source emits infrared-type radiant energy symmetrically into the two portions. Each portion incorporates a curved reflective surface which reflects incident infrared onto a respective sensor. Each sensor has a filter which passes a different selected band of energy. A fluid, such as gas being sensed, passes laterally through the chamber.

73 Claims, 2 Drawing Sheets

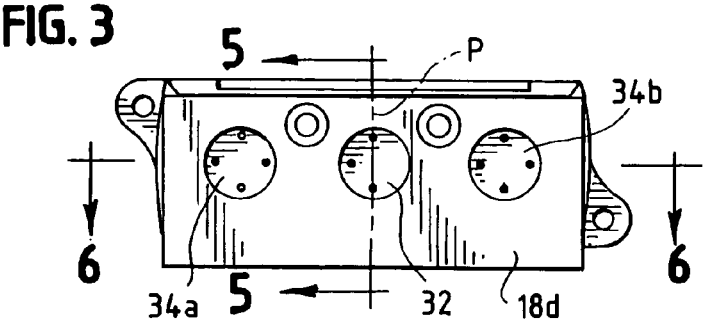
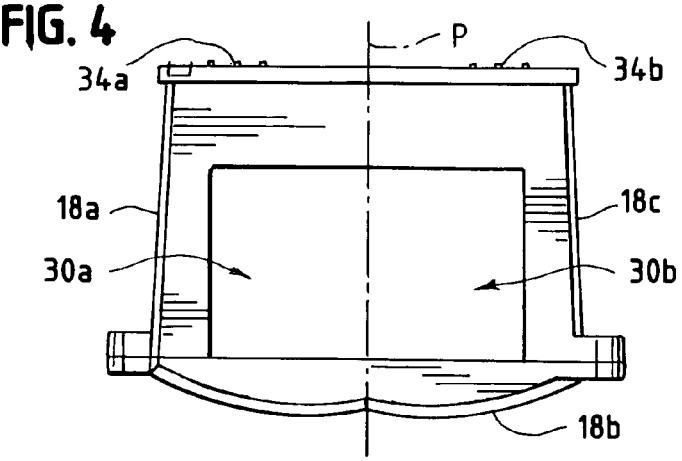
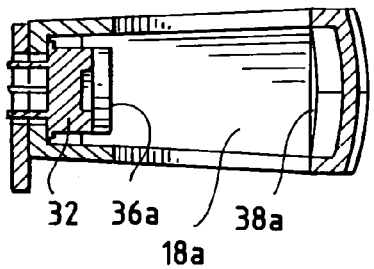
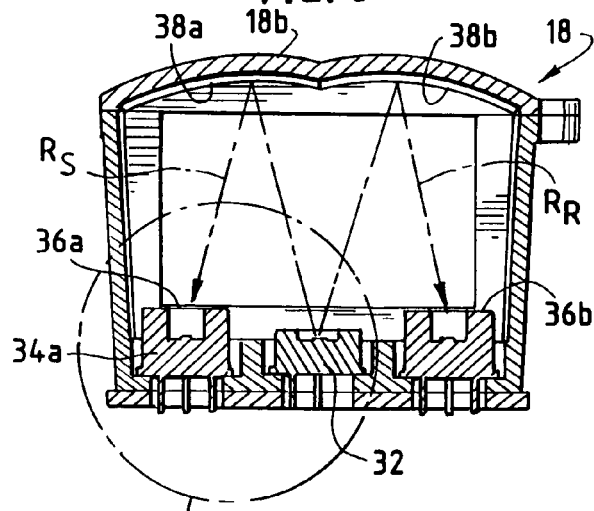
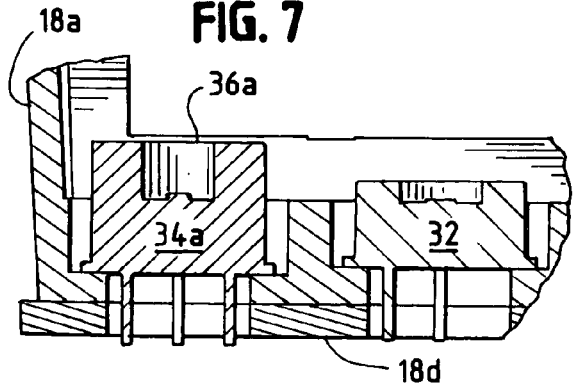

CHAMBER FOR GAS DETECTOR

FIELD OF THE INVENTION

The invention pertains to gas detectors. More particularly, the invention pertains to gas detectors having a reference chamber, a sensing chamber and a common source of radiation.

BACKGROUND OF THE INVENTION

Non-dispersive infrared (NDIR) gas detectors are known for sensing the presence and concentration of various gases. Many known NDIR-type detectors are more in the nature of laboratory instruments than relatively small, rugged and convenient sensors for use in the field. As a result, many of the known detectors have suffered from complexity and relatively high cost.

Airborne contaminants such as particulate matter or water vapor can adversely affect detector outputs. Filtering is known to exclude particular matter. Filtering, however, may not exclude water vapor. Other known NDIR-type detectors have attempted to address environmental conditions, such as condensation of water vapor in the gas being sampled by heating the sample chamber electrically. Such heaters and their power supplies result in added bulk, weight and cost in the respective detectors.

There thus continues to be a need for NDIR-type detectors which do not require either electrical heating, or large amounts of space, electromechanical choppers and the like, or, complex processing circuitry. Preferably, such chambers could be inexpensive to manufacture, and require little or no adjustment or field maintenance.

BRIEF DESCRIPTION OF THE DRAWINGS

FIG. 3 is an end elevational of the housing of FIG. 2;

FIG. 4 is a top plan view of the chamber of FIG. 2;

FIG. 5 is a sectional view taken along plane 5—5 of FIG. 3;

FIG. 6 is a sectional view taken along plane 6—6 of FIG. 3; and

FIG. 7 is an enlarged view of a portion of the chamber of FIG. 6.

DETAILED DESCRIPTION OF THE EMBODIMENTS

Figure 1:
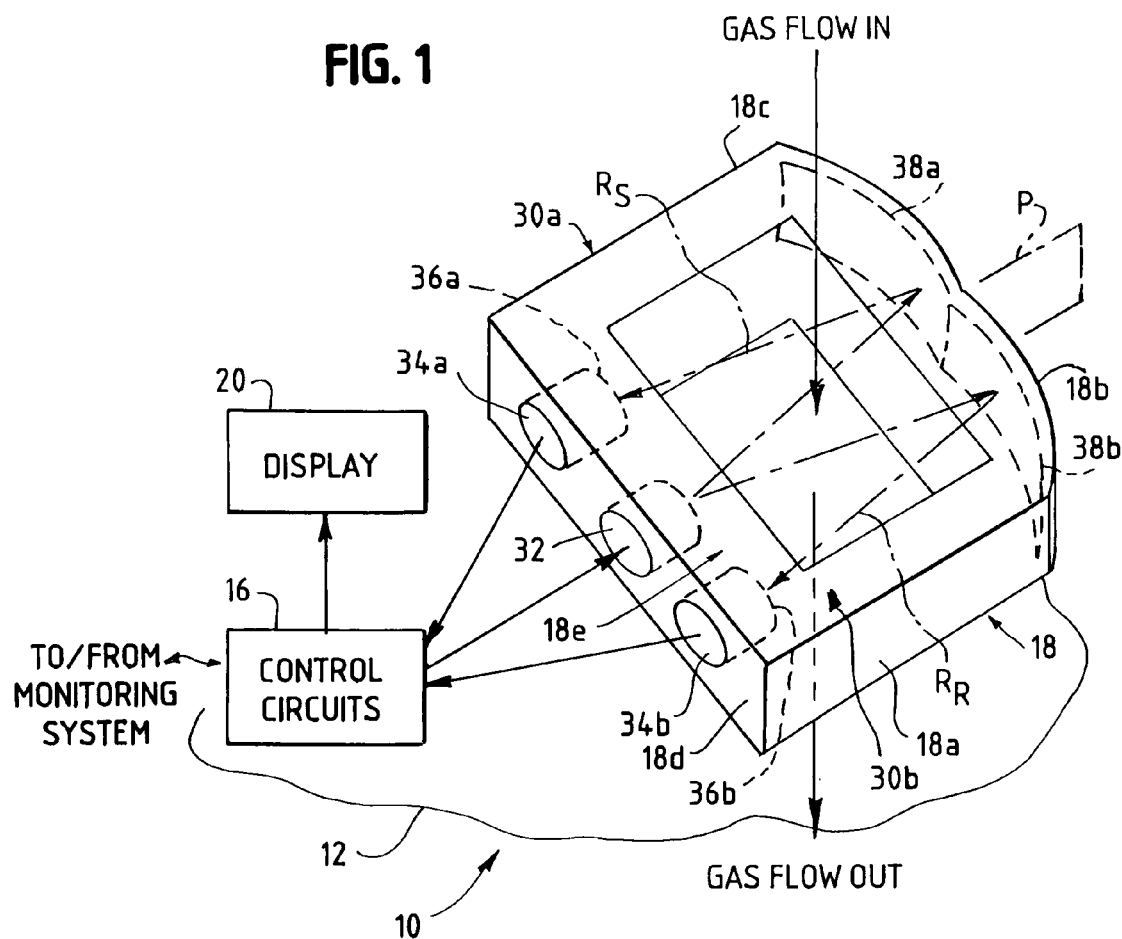
FIG. 1 is an over-all view of a detector in accordance with the present invention, partly broken away.
Figure 2:
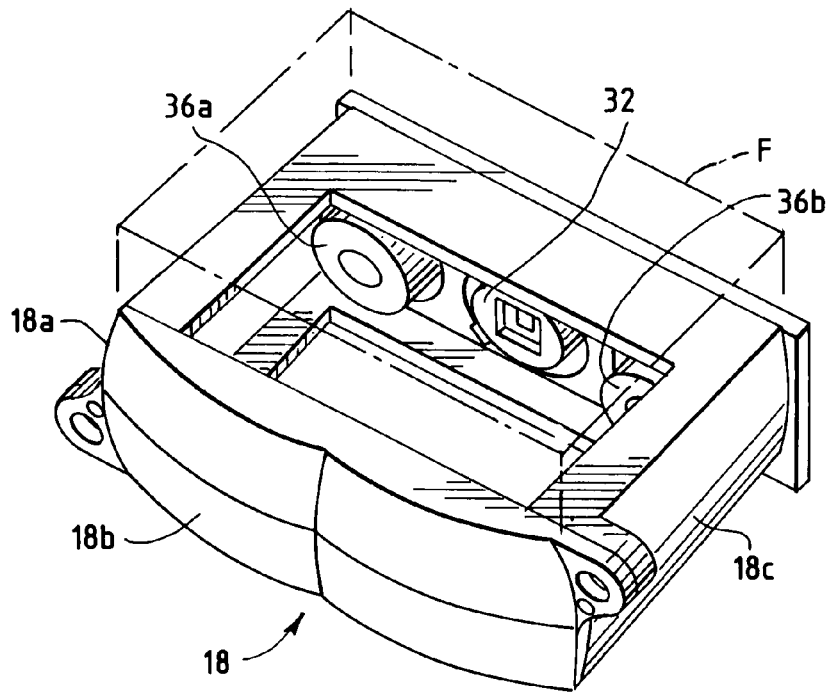
FIG. 2 is a perspective view of a portion of the detector of FIG. 1.

While embodiments of this invention can take many different forms, specific embodiments thereof are shown in the drawings and will be described herein in detail with the understanding that the present disclosure is to be considered as an exemplification of the principles of the invention and is not intended to limit the invention to the specific embodiment illustrated.

A gas detector in accordance with the invention can be fabricated as a smaller, light weight, stand alone portable device that has no adjustments. Such detectors can, alternately, be part of a larger monitoring system.

A sensor design which embodies the invention is suitable for use in NDIR-type gas detectors. This structure includes a sensing and a reference chamber that are open to each other. The reference chamber is a mirror image of the sensing chamber relative to a plane that passes between them.

The sensing chamber has a radiant energy sensor with a filter that passes the band of energy associated with the gas to be detected. The reference chamber has a radiant energy sensor with a filter that passes a band of energy not associated with the gas to be detected. An opening for lateral entry of the gas being monitored is preferably symmetrically located between the sensing and reference chambers.

The sensing and reference chambers each include a concave reflective surface such that substantially only one reflection of light occurs between an emitter and the associated sensor. The path length of the light rays is substantially similar.

One advantage of the reference chamber being a mirror image of the sensing chamber is that environmental conditions are likely to affect each chamber the same. For example, any water vapor in the gas sample can be expected to condense uniformly on the reflective surfaces, thus affecting performance of each chamber equally. Thus, compensation for such environmental conditions is more readily achieved. Further, each chamber has a similar concave reflective surface that focuses a substantial amount of the light rays to the associated sensor.

FIG. 1 illustrates detector 10 which has a housing 12. Housing 12 carries control circuits 16, which could be implemented in part with a processor and executable instructions. Housing 12 also carries housing 18 for sensing a concentration of a selected gas.

Display 20, driven by signals from control circuit 16 could display gas concentration, for example, parts per million or the like all without limitation. It will be understood that the characteristics of the display 20 are not a limitation of the present invention.

Housing 18 is formed with bounding side walls 18a, b, c, d which bound on interior region 18e. The side walls define a sensing chamber or portion indicated generally at 30a and a reference chamber or portion indicated generally at 30b. The sensing and reference chambers 30a, b are open to each other along a common plane P, see FIG. 3.

Plane P corresponds to plane 5—5 and is generally parallel to a direction of flow of gas into/out of detector 10.

Reference chamber 30b is a mirror image of sensing chamber 30a. A shared emitter 32 is located on the common plane P between the sensing and reference portions 30a, b. The housing 18 can be formed of a variety of materials, including cured plastic resin, all without limitation of the present invention.

Sensors 34a and 34b are carried on side wall 18d. Each of the sensors 34a, b has associated therewith a respective optical filter 36a, b. The filter 36a passes a band of energy associated with the gas to be detected. The filter 36b passes a band of energy not associated with the gas to be detected. Sensors 34a, b and their respective filters 36a, b are symmetrically located relative to plane P and emitter 32.

The filter 36a for the sensing chamber 30a passes a wavelength(s) known to be absorbable by the gas(s) being used. Filter 30b, for reference chamber 30b passes a wavelength(s) not absorbed by the gas(s) being sensed.

Each of the chambers 30a, b also includes a curved concave reflector 38a, 38b. The reflector could be spherical or parabolic all without limitation of the present invention. Other curved surfaces could also be used.

Radiant energy emitted from emitter 32 is equally incident upon reflector 38a, 38b after passing through the respective sensing chamber 30a or reference chamber 30b.

On reflection off of the respective surfaces 38a, b, the radiant energy passes through respective filter 36a, b and is incident upon respective sensor 34a, b which converts same to a corresponding electrical signal. Those signals are in turn coupled to control circuit 16.

Representative types of gases suitable for being sensed using gas sensor 18 include hydrocarbons such as carbon monoxide, carbon dioxide, combustible gases such methane, ethane and the like as well as water vapor. It will be understood that the gas being sensed is not a limitation of the invention.

Emitter 32 is selected to have a radiant energy output of a wavelength absorbable by the type of gas to be sensed. For example, emitters having wave lengths in the range of 3 to 5 microns are suitable for sensing hydrocarbons such as carbon monoxide or carbon dioxide. Other wave lengths would be used, as would be understood by those of skill in the art, for sensing different gases.

The emitter 32 could be implemented using a light bulb, a light emitting diode, a laser diode or the like all without limitation. It will also be understood that the particular emitter of choice in a given gas sensor is not a limitation of the invention.

It will also be understood that the bounded open region 18e of housing 18 through which the gas flow passes could be closed with one or more gas receiving filters F, such as a semi-permeable membrane. Use of a filter such as a membrane reduces or limits the velocity of gas flow through the housing 18 such that movement therein is by diffusion only. Further, use of a filter excludes undesirable incident particulate matter. It will be understood that a variety of filter configurations could be used without departing from the spirit and scope of the present invention.

The gas sensor 18 has a structure which is particularly advantageous in that there is by and large only a single reflection of radiant energy emitted at emitter 32 before being incident on one of the respective sensors 34a, b. This single reflection takes place at the respective reflector 38a, b. As a result, the distance traversed by the radiant energy in both the sensing chamber and the reference chamber 38a, b is substantially identical in both instances. The structure is also advantageous in that the concave reflective surfaces 38a, b focus a substantial portion of the incident radiant energy onto the respective sensor 34a, b.

The housing 18 is also advantageous in that undesirable environmental conditions, such as water vapor in the inflowing gas can be expected to affect both reflectors 38a, b similarly. The debilitating effects of the condensation on the respective reflectors can be substantially eliminated by forming a ratio of the outputs from sensors 34a, b.

The fabrication of reflected surfaces 38a, b is not complicated by having to form apertures therein for an inflow of the gas to be sensed. Rather, the gas to be sensed enters the gas sensor 18 generally parallel to the plane P, and, more or less perpendicular to the direction of transmission of the radiant energy from emitter 32 across the sensing chamber and reference chamber 30a, b.

FIGS. 2–7 illustrate further details of the chamber 18. The incident and reflected radiation for sensing and reference purposes $R_S$, $R_R$ travel substantially the same distances in housing 18. Only a single reflection is required between source 32 and sensors 34a, b as the radiant energy travels through the gas(s) being sensed.

Housing 18 can be molded of a variety of commercially available resins without limitation. The molding process defines the curves of reflectors 38a, b as well as mounting surfaces for emitter 32 and sensors 34a, b. There are no adjustments as none are needed.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. A gas sensor comprising:
    a housing, the housing defining first and second, substantially mirror image portions, the portions abut one another along a common plane and are open to one another;
    a gas inflow portal laterally located relative to portions; and
    a centrally located source of radiant energy.

2. A sensor as in claim 1 where the gas inflow portal is substantially perpendicular to the common plane.

3. A sensor as in claim 2 which includes a filter which overlies the portions.

4. A sensor as in claim 3 where the source is located on the common plane.

5. A sensor as in claim 1 with the inflow portal symmetrically located relative to the common plane.

6. A sensor as in claim 1 which includes a gas outflow portal, displaced from the inflow portal by the portions and symmetrically located relative to the portions.

7. A sensor as in claim 1 where each of the portions includes a reflective member.

8. A sensor as in claim 7 where the reflective members are curved.

9. A gas sensor comprising:
    a housing, the housing defining first and second substantially mirror image portions, the portions abut one another along a common plane and are open to one another;
    a gas inflow portal laterally located relative to portions; and
    which includes a filter which overlies the portions;
    where the filter substantially reduces fluid flow velocity in the portions.

10. A gas sensor comprising:
    a housing, the housing defining first and second substantially mirror image portions, the portions abut one another along a common plane and are open to one another;
    a gas inflow portal laterally located relative to portions; and
    which includes a filter which overlies the portions;
    where, except for diffusion, the filter reduces velocity of ambient gases in the portions substantially to zero.

11. A gas sensor comprising:
    a housing, the housing defining first and second substantially mirror image portions, the portions abut one another along a common plane and are open to one another;
    a gas inflow portal laterally located relative to portions; and
    which includes first and second sensing elements, one associated with each portion.

12. A sensor as in claim 11 with the elements carried by the housing, symmetrically located relative to the common plane.

13. A sensor as in claim 12 where the source directs radiant energy substantially symmetrically relative to the common plane and in a plane generally perpendicular thereto.

14. A gas sensor comprising:
a housing, the housing defining first and second substantially mirror image portions, the portions abut one another along a common plane and are open to one another;
a gas inflow portal laterally located relative to portions;
where each of the portions includes a reflective member; and
where radiant energy crosses the portions with only a single reflection.

15. A gas sensor comprising:
a housing, the housing defining first and second substantially mirror image portions, the portions abut one another along a common plane and are open to one another;
a gas inflow portal laterally located relative to portions;
where the source directs radiant energy substantially symmetrically relative to the common plane and in a plane generally perpendicular thereto; and
where radiant energy crosses the portions with only a single reflection.

16. A chamber comprising:
a first sensing device and a second sensing device;
an emitter that transmits light;
a first concave reflective surface;
a second concave reflective surface;
the first sensing device receives at least some first light reflected from the first concave reflective surface and the second sensing device receives at least some second light reflected from the second concave reflective surface;
at least one gas entry opening;
where the at least one gas entry opening is positioned such that entering gas will enter into the first light and second light at substantially the same time.

17. A chamber comprising:
a first sensing device and a second sensing device;
an emitter device that transmits light;
a first concave reflective surface;
a second concave reflective surface;
the first sensing device receives at least some first light reflected from the first concave reflective surface and the said second sensing device receives at least some second light reflected from the said second concave reflective surface;
at least one gas entry opening;
where the at least one gas entry opening is located such that the gas entering the chamber will reach both the first concave reflective surface and the second concave reflective surface at substantially the same time.

18. A chamber comprising:
a first sensing device and a second sensing device;
an emitter that transmits light;
a first concave reflective surface;
a second concave reflective surface;
the first sensing device receives at last some first light reflected from the first concave reflective surface and the second sensing device receives at least some second light reflected from the second concave reflective surface;
at least one gas entry opening;
where the at least one gas entry opening is positioned in the chamber such that water in the gas entering the chamber will condense substantially equally on both the first concave reflective surface and the said second concave reflective surface at substantially the same time.

19. A chamber as in claim 18 wherein the first concave reflective surface is substantially identical to the second concave reflective surface.

20. A chamber as in claim 18 where the at least one gas entry opening is covered with filter material to excluded dust.

21. A chamber as in claim 18 where the first light and second light are substantially the same.

22. A chamber as in claim 21 where the first light and the second light vary by substantially the same amount due to water condensing on both concave reflective surfaces.

23. A folded beam, gas sensing chamber comprising:
at least one curved reflective surface;
an emitter; and
at least one sensor of emitted light reflected just once; and
first and second optical filters for producing a gas related radiant energy beam and a reference beam.

24. A chamber as in claim 23 with a housing that has first and second mirror image regions, respectively, a sensing region and a reference region.

25. A chamber as in claim 24 where gas to be sensed flows into both regions substantially simultaneously.

26. A gas detector comprising:
a first sensing device and a second sensing device;
an emitter;
at least a first reflective surface that reflects at least first light rays from the emitter, a portion of said first light rays are received by a first sensing device;
at least a second reflective surface that reflects at least second light rays from the emitter, a portion of second light rays are received by a second sensing device;
where the at least first and second reflective surfaces are substantially a mirror image of one another relative to a common plane; and
at least one gas entry opening.

27. A gas detector as in claim 26 where the first sensing device senses a predetermined gas.

28. A gas detector as in claim 26 where the second sensing device senses a different gas than the first sensing device.

29. A gas detector as in claim 28 where the second sensing device comprises a reference device for compensating the first sensing device.

30. A gas detector as in claim 26 where the reflective surfaces focus at least portions of the light from the emitter to the sensing devices.

31. A gas detector as in claim 26 wherein the reflective surfaces are formed of gold or chrome.

32. A gas detector as in claim 26 where the two reflective surfaces are separate parts that are assembled to form the reflective surfaces within the chamber.

33. A gas detector as in claim 26 where the reflective surfaces are integrally formed.

34. A gas detector as in claim 26 where the gas entry opening includes a filter to exclude contaminants.

35. A gas detector as in claim 26 where the chamber has more than one gas entry opening.

36. A gas detector as in claim 26 where the chamber parts are constructed of plastic.

37. A gas detector as in claim 26 where the reflective surfaces are coated with a material to prevent degrading of the reflectivity.

38. A gas detector as in claim 26 where the first and second sensing devices are on opposite sides of the emitter.

39. A gas detector as in claim 26 where the first and second sensing devices have at least partly surrounding light collectors to increase the light rays focused thereon.

40. A gas detector as in claim 26 where the light collectors are reflectors.

41. A gas detector as in claim 26 where the light collectors are lenses.

42. A gas detector as in claim 26 where at least one of the emitter, first sensing device, or second sensing device has a lens to focus light.

43. A gas detector as in claim 26 where the emitter has a reflector around at least a portion of it to focus light.

44. A gas detector comprising:
a housing;
control circuits carried by the housing;
a diffusion chamber, carried by the housing, the chamber having sensing and reference portions;
a reflector symmetrically located relative to the portions;
a gas inflow port, on the housing, oriented to enable inflowing ambient gas to diffuse substantially symmetrically into the portions.

45. A detector as in claim 44 where the control circuits include executable instructions to compensate for undesired gas born contaminants.

46. A detector as in claim 45 with the contaminants comprising water vapor.

47. A detector as in claim 44 with the portions open to one another along a common plane.

48. A detector as in claim 47 where the inflow port is symmetrically located relative to the common plane.

49. A detector as in claim 47 where the inflowing gas moves in a direction generally parallel to the common plane.

50. A detector as in claim 49 which includes radiant energy beams that extend generally perpendicular to the common plane.

51. A detector as in claim 50 where the beams each exhibit a single reflection.

52. A detector a in claim 51 with a first beam extending across and reflected in one portion with a second beam extending across and reflected in the other portion.

53. A detector as in claim 44 where the sensing and reference portions are symmetrical.

54. A method comprising:
providing inflowing gas sensing and reference regions at the same time;
enabling the gas to diffuse between the regions across a common plane;
projecting a sensing beam across the sensing region;
projecting a reference beam across the reference region;
sensing selected wavelengths in the beams subsequent to transversing the regions; and
establishing a concentration of a selected constituent of the gas.

55. A method as in claim 54 which includes reflecting the beams across the respective region.

56. A method as in claim 54 where the beams are projected from a common location.

57. A method as in claim 54 where the beams are sensed at two different locations.

58. A method as in claim 57 where the beams are each filtered prior to being sensed.

59. A sensor comprising:
first and second adjacent reflectors on each side of a plane therebetween;
a source of radiant energy substantially located on the plane, the radiant energy directly incident on each of the reflectors to thereby provide indicia of the presence of a predetermined fluid between the source and at least one of the reflectors.

60. A sensor as in claim 59 which includes a fluid inflow portal.

61. A sensor as in claim 60 where inflowing fluid simultaneously flows into first and second regions on each side of the plane.

62. A sensor as in claim 61 which includes a gas outflow portal, displaced from the inflow portal.

63. A sensor as in claim 60 with the inflow portal symmetrically located relative to the plane.

64. A sensor as in claim 60 which includes a filter between the inflow portal and the reflectors.

65. A sensor as in claim 64 where the filter substantially reduces the fluid flow velocity in a region between the source and the reflectors.

66. A sensor as in claim 61 where, except for diffusion, the filter reduces velocity of ambient fluids in the region between the source and the reflectors substantially to zero.

67. A sensor as in claim 60 including a housing which carries the source and the reflector as well as control circuitry which receives the indicia.

68. A sensor as in claim 67 where fluid inflow, through the portal, is substantially parallel to the plane.

69. A sensor as in claim 68 where the indicia correspond to a reference indicator and a sensed fluid indicator, the indicators are symmetrically located relative to the plane and coupled to the control circuitry.

70. A sensor as in claim 59 where the reflectors are curved.

71. A sensor as in claim 59 which includes first and second spaced apart sensing elements, one associated with each reflector.

72. A sensor as in claim 71 where respective radiant energy reflected once off of a respective reflector is incident on a respective sensing element.

73. A sensor as in claim 72 which includes an optical filter associated with one of the sensors, the respective sensor emitting one of a reference signal or a gas concentration indicating signal.

* * * * *